(12) United States Patent
DeBord

(10) Patent No.: US 10,987,205 B2
(45) Date of Patent: Apr. 27, 2021

(54) SURGICAL SYSTEMS AND TRAYS

(71) Applicant: BIOMET 3I, LLC, Palm Beach Gardens, FL (US)

(72) Inventor: Jeffrey T. DeBord, Worthington, OH (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 0 days.

(21) Appl. No.: 16/591,218

(22) Filed: Oct. 2, 2019

(65) Prior Publication Data
US 2020/0107920 A1 Apr. 9, 2020

Related U.S. Application Data

(60) Provisional application No. 62/742,775, filed on Oct. 8, 2018, provisional application No. 62/747,199, filed
(Continued)

(51) Int. Cl.
*A61C 19/02* (2006.01)
*B65D 25/10* (2006.01)

(52) U.S. Cl.
CPC ............ *A61C 19/02* (2013.01); *B65D 25/108* (2013.01)

(58) Field of Classification Search
CPC ........ A61C 19/02; A61C 3/04; B65D 25/108; A61B 50/20; A61B 50/33; A61B 50/24;
(Continued)

(56) References Cited

U.S. PATENT DOCUMENTS 2,438,989 A * 4/1948 Billman ................ B25B 1/2452
269/221
3,603,551 A * 9/1971 Peterson ............... A47F 7/0028
248/314
(Continued)

FOREIGN PATENT DOCUMENTS

DE 1038714 9/1958
EP 1142537 10/2001
(Continued)

OTHER PUBLICATIONS

"European Application Serial No. 19202063.4, Partial European Search Report dated Dec. 19, 2019", 14 pages.
(Continued)

*Primary Examiner* — Jennifer E. Novosad
(74) *Attorney, Agent, or Firm* — Schwegman Lundberg & Woessner, P.A.

(57) ABSTRACT

An instrument retaining element for a surgical tray such as dental tray for use in a dental surgical procedure. The retaining element can have a first part defining a plurality of receptacles therein. The plurality of receptacles configured to receive a first shank section of a plurality of dental surgical instruments. The first part defines a first part of a channel that communicates with two or more of the plurality of receptacles. The retaining element can have a second part connected to the first part and having a U-shape in cross-section. The second part defines a second part of the channel that communicates with the first part of the channel and the plurality of receptacles. The second part of the channel can be configured to elastically expand to receive and retail a second shank section of the plurality of dental surgical instruments.

20 Claims, 13 Drawing Sheets

Related U.S. Application Data on Oct. 18, 2018, provisional application No. 62/811,789, filed on Feb. 28, 2019.

(58) Field of Classification Search
CPC .... Y10T 29/49826; B01L 9/06; A47F 7/0028; B25H 3/006; B25H 3/04; B25H 3/06
USPC .... 211/85.13, 85.18, 70.6, 69; 206/63, 63.5, 206/368, 369
See application file for complete search history.

(56) References Cited

U.S. PATENT DOCUMENTS

| | | | | |
|---|---|---|---|---|
| 3,643,812 | A * | 2/1972 | Mander | B65D 25/108 211/74 |
| 4,212,390 | A * | 7/1980 | Raczkowski | A61B 17/105 206/339 |
| 4,253,830 | A * | 3/1981 | Kazen | A61C 3/04 206/368 |
| 4,535,897 | A * | 8/1985 | Remington | B25H 3/00 211/70.6 |
| 4,690,285 | A * | 9/1987 | Stone | B43M 99/008 211/70.6 |
| 5,004,103 | A * | 4/1991 | Connors | B25H 3/02 206/372 |
| 5,108,287 | A * | 4/1992 | Yee | A61C 3/04 206/369 |
| 5,128,105 | A * | 7/1992 | Berthold | B01L 9/06 422/561 |
| 5,172,810 | A * | 12/1992 | Brewer | A61C 3/04 206/368 |
| 5,271,501 | A * | 12/1993 | Chen | B25H 3/06 206/373 |
| 5,368,164 | A * | 11/1994 | Bennett | B25H 3/003 206/373 |
| 5,490,975 | A * | 2/1996 | Dane | A61L 2/26 206/379 |
| 5,525,314 | A * | 6/1996 | Hurson | A61C 3/04 206/369 |
| 5,544,744 | A * | 8/1996 | Oman | B25H 5/00 206/319 |
| 5,544,747 | A * | 8/1996 | Horn | B25H 3/04 206/378 |
| 5,573,116 | A * | 11/1996 | Zink | B25H 3/06 206/377 |
| 5,913,422 | A * | 6/1999 | Cote | A61L 2/26 206/210 |
| 6,079,559 | A * | 6/2000 | Lee | A47F 5/0006 206/372 |
| 6,099,812 | A * | 8/2000 | Allen | A61L 2/26 206/370 |
| 6,109,446 | A * | 8/2000 | Foote | A45D 44/04 206/372 |
| 6,345,873 | B1 * | 2/2002 | Kim | F16L 3/223 248/68.1 |
| 6,431,373 | B1 * | 8/2002 | Blick | B25H 3/003 206/378 |
| 6,547,077 | B1 * | 4/2003 | Budert | B25H 3/003 206/379 |
| 6,568,544 | B1 * | 5/2003 | Lafond | B01L 9/06 211/74 |
| 7,246,704 | B2 * | 7/2007 | Brunson | B25H 3/003 206/372 |
| 7,258,240 | B2 * | 8/2007 | Wescott, III | B01L 9/06 211/74 |
| 7,322,470 | B2 * | 1/2008 | Brunson | B25H 3/003 206/372 |
| 7,527,147 | B2 * | 5/2009 | Corcoran | A61C 7/12 206/369 |
| 7,857,129 | B2 * | 12/2010 | Iaconi-Forrer | A61B 50/20 206/339 |
| 8,069,998 | B2 * | 12/2011 | Thomas | A61L 2/26 211/85.13 |
| 8,215,480 | B2 * | 7/2012 | Qian | B01L 9/06 206/45.2 |
| 8,336,709 | B1 * | 12/2012 | Geibel | B25H 3/06 206/350 |
| D742,029 | S * | 10/2015 | Rowe | D24/229 |
| 9,149,336 | B2 * | 10/2015 | Dane | A61L 2/26 |
| 9,744,013 | B2 * | 8/2017 | Kerboul | A61C 3/04 |
| 10,575,933 | B2 * | 3/2020 | Berg | A61B 50/30 |
| 2001/0010291 | A1 * | 8/2001 | Hu | B25H 3/003 206/377 |
| 2002/0153336 | A1 * | 10/2002 | Wang | A47F 7/0028 211/60.1 |
| 2004/0144739 | A1 * | 7/2004 | Marek | B25H 3/04 211/70.6 |
| 2004/0238466 | A1 * | 12/2004 | Shiao | B25H 3/04 211/70.6 |
| 2010/0065456 | A1 * | 3/2010 | Junk | A61B 50/20 206/363 |
| 2013/0334083 | A1 * | 12/2013 | Bugnard | A61B 50/33 206/370 |
| 2015/0129524 | A1 * | 5/2015 | Cushion | A61B 50/20 211/85.13 |
| 2016/0368133 | A1 * | 12/2016 | Welfel | B25H 3/06 |
| 2017/0217637 | A1 * | 8/2017 | Auerbach | A61M 5/008 |
| 2018/0079572 | A1 * | 3/2018 | van den Dries | A61H 37/00 |
| 2019/0283234 | A1 * | 9/2019 | Ko | B25H 3/025 |
| 2020/0107912 | A1 * | 4/2020 | Schlueter | A61C 3/04 |
| 2020/0107920 | A1 * | 4/2020 | DeBord | A61B 50/33 |

FOREIGN PATENT DOCUMENTS

| | | |
|---|---|---|
| JP | 2001315748 | 11/2001 |
| WO | 2012084199 | 6/2012 |
| WO | 2016142331 | 9/2016 |

OTHER PUBLICATIONS

U.S. Appl. No. 16/591,208, filed Oct. 2, 2019, Surgical Systems and Trays.

"European Application Serial No. 19202067.5, Extended European Search Report dated Feb. 4, 2020", 8 pages.

"European Application Serial No. 19202063.4, Extended European Search Report dated Mar. 31, 2020", 12 pages.

* cited by examiner

SURGICAL SYSTEMS AND TRAYS

CLAIM OF PRIORITY

This application claims the benefit of U.S. Provisional Patent Application Ser. No. 62/742,775, filed on Oct. 8, 2018, and U.S. Provisional Patent Application Ser. No. 62/747,199, filed on Oct. 18, 2018, and U.S. Provisional Patent Application Ser. No. 62/811,789, filed on Feb. 28, 2019, the benefit of priority of each of which is claimed hereby, and each of which are incorporated by reference herein in its entirety.

FIELD

The present invention relates to surgical systems and, in particular, to surgical trays for housing such systems.

BACKGROUND

Dental surgical implants are medical devices that are designed to replace the function of a tooth. Following the loss or removal of a tooth an implantable portion of the dental surgical implant is surgically implanted into the alveolar bone where various biological processes lead to the development of new bone on the implant surface rendering the device capable of supporting loading forces, including those experienced during mastication. For most dental surgical implant systems in current use, the implantable portion (sometimes referred to simply as the implant) is only one component required for restoring the function of a lost tooth. Additional components are required to accomplish the restoration. These include devices designed to attach to the implantable portion (abutments) and support the dental prosthesis (crown). These components include various designs, sizes and mechanisms for mating together. When properly combined, the implant-abutment-crown assembly (which can be formed by the dental surgical implant systems described herein) is capable of providing the function of a natural tooth for many years.

Surgical trays (commonly also called a cassette) is known for supplying dental surgical implant systems and for supplying supporting systems of tools and other surgical equipment used for the procedure. These supporting systems (sometimes simply called dental surgical equipment herein) include surgical tools (e.g., drills), instruments, etc. However, the functionality of the packaging in supporting the surgical procedure to make the procedure easier, more ergonomic and less time consuming for the dentist has been limited. For example, it can often be difficult for the dentist to be able to instantly identify from his supply of dental surgical equipment the correct size and type of tool needed, and then be able to conveniently obtain the correct tool once it is identified.

OVERVIEW

Medical dentistry is a complex and demanding therapeutic discipline where both functionality and esthetics are required as are expected outcomes. Although the systems and trays described illustrate dental surgical equipment, it should be understood that in other examples the systems and trays disclosed can include dental surgical implants and other components used in the surgical procedure.

According to one aspect, the present disclosure relates to a dental tray that facilitates organization of the surgical procedure enabling faster and more accurate visual selection of the proper tool, for example. The dental tray can include a hinged design with multiple possible positioning configurations that can facilitate ease of use, use in a reduced space environment, etc. According to yet further examples, the tray can be configured such that the sharp ends of tools can be angled away from the user to minimize the chances of unwanted contact with a sharp. In further examples, the dental tray can include a plurality of grommets as part of a tray insert that are interconnected by a channel. This configuration can improve ease of cleaning and holding stability of dental surgical equipment and/or dental surgical implants of different geometry (e.g., diameters). In some examples, tray inserts can be removable from the tray and can be designed with supports to facilitate storage space underneath for surgical tools. The tray inserts can have translucent or transparent areas to increase visibility of the surgical tools stored under the tray inserts. In further examples, the dental tray can be powered (e.g., has a drive mechanism) to move the dental tray along a predetermined cleaning pathway where the dental tray and the surgical instruments are cleaned according to a pre-defined cleaning protocol.

To further illustrate the apparatuses and systems disclosed herein, the following non-limiting examples are provided:

In Example 1, an instrument retaining element for a dental tray for use in a surgical procedure, can optionally comprise: a first portion defining a plurality of receptacles therein, the plurality of receptacles configured to receive a first shank section of a plurality of surgical instruments, wherein the first portion defines a first part of a channel that communicates with two or more of the plurality of receptacles; and a second portion connected to the first portion and having a U-shape in cross-section, wherein the second portion defines a second part of the channel that communicates with the first part of the channel and the plurality of receptacles, and wherein the second part of the channel is configured to elastically expand to receive and retain a second shank section of the plurality of surgical instruments when the first section of the plurality of surgical instruments are received in the plurality of receptacles.

In Example 2, the retaining element of Example 1, wherein the first portion can optionally be shaped as a flange and is removable from and insertable into another portion of the tray insert.

In Example 3, the retaining element of any one of Examples 1-2, wherein the first portion can have an exterior facing surface that comprises a stop for the plurality of surgical instruments when the plurality of surgical instruments are inserted in the tray insert.

In Example 4, the retaining element of any one of Examples 1-3, wherein the second portion can have a first opening for the channel at a first end thereof.

In Example 5, the retaining element of Example 4, wherein the first portion can have a second opening that comprises a slit for the channel.

In Example 6, the retaining element of any one of Example 4 or 5, wherein at least one of the first opening and the second opening can allow for access to the channel for cleaning.

In Example 7, the retaining element of any one of Examples 1-6, wherein the second portion can be configured to exert a force on the plurality of surgical instruments to retain the plurality of surgical instruments within the second part of the channel.

In Example 8, the retaining element of Example 7, wherein the force can be exerted by elastic expansion of the second portion upon receiving the plurality of surgical instruments in the second part of the channel.

In Example 9, a medical tray for a surgical procedure, can optionally comprise: a housing; and one or more tray inserts configured to be received within the housing, wherein each of the one or more tray inserts includes an instrument retaining portion that is configured to receive and retain a plurality of surgical instruments via a plurality of receptacles and a channel formed therein, wherein the channel communicates with the plurality of receptacles and is expandable to receive one or more of the plurality of surgical instruments.

In Example 10, the medical tray of Example 9, wherein the instrument retaining portion is configured to exert a force on the plurality of surgical instruments to retain the plurality of surgical instruments within the channel.

In Example 11, the medical tray of any one of Examples 9-10, wherein the instrument retaining portion optionally can comprise: a first portion defining the plurality of receptacles and defining a first part of the channel; a second portion connected to the first portion and having a U-shape in cross-section, wherein the second portion defines a second part of the channel that communicates with the first part of the channel and the plurality of receptacles, and wherein the second part of the channel is configured to receive a second section of the plurality of surgical instruments when a first section of the plurality of surgical instruments are received in the plurality of receptacles.

In Example 12, the medical tray of Example 11, wherein the first portion is shaped as a flange and is removable from and insertable into another portion of the tray insert.

In Example 13, the medical tray of any one of Examples 11-12, wherein the first portion can have an exterior facing surface that comprises a stop for the plurality of surgical instruments when the plurality of surgical instruments are inserted in the tray insert.

In Example 14, the medical tray of any one of Examples 11-13, wherein the second portion can have a first opening for the channel at a first end thereof.

In Example 15, the medical tray of Example 14, wherein the first portion can have a second opening that comprises a slit for the channel.

In Example 16, the medical tray of any one of Example 14 or 15, wherein at least one of the first opening and the second opening can allow for access to the channel for cleaning.

In Example 17, the medical tray of any one of Examples 11-16, wherein the second portion can be configured to exert a force on the plurality of surgical instruments to retain the plurality of surgical instruments within the second part of the channel.

In Example 18, the medical tray of Example 17, wherein the force can be exerted by elastic expansion of the second portion upon receiving the plurality of surgical instruments in the second part of the channel.

In Example 19, the medical tray of Example 11, wherein the channel and the plurality of receptacles can have corresponding openings at a first major surface of the instrument retaining element.

In Example 20, a medical tray for a surgical procedure, can optionally comprise: a housing; and one or more tray inserts configured to be received within the housing, wherein each of the one or more tray inserts includes an instrument retaining element having a plurality of receptacles and a channel formed therein, wherein the channel communicates with the plurality of receptacles, wherein instrument retaining element is configured to receive a plurality of surgical instruments via the plurality of receptacles and the channel, and wherein a portion of the instrument retaining element that defines the channel is configured to exert a force on the plurality of surgical instruments to retain the plurality of surgical instruments within the channel.

In Example 21, the system of any one or any combination of Examples 1-20 can optionally be configured such that all elements or options recited are available to use or select from.

These and other examples and features of the present systems will be set forth in part in the following Detailed Description. This Overview is intended to provide non-limiting examples of the present subject matter—it is not intended to provide an exclusive or exhaustive explanation. The Detailed Description below is included to provide further information about the present systems.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to medical systems and medical trays such as dental systems and dental trays. The subject matter is not limited to dentistry. The dental trays, for example, can be used to house and carry dental surgical equipment and/or dental surgical implant systems, for example.

Figure 1A:
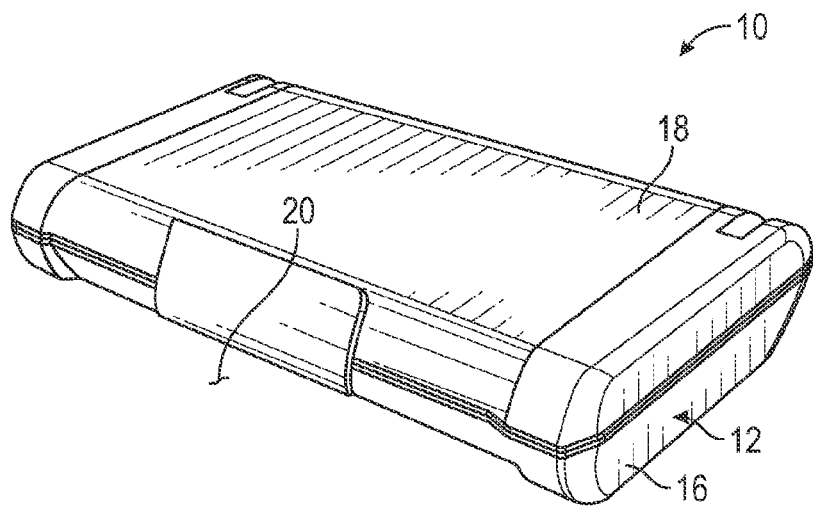
FIG. 1A is a perspective view of a dental tray in a closed position according to an example of the present disclosure.
Figure 1B:
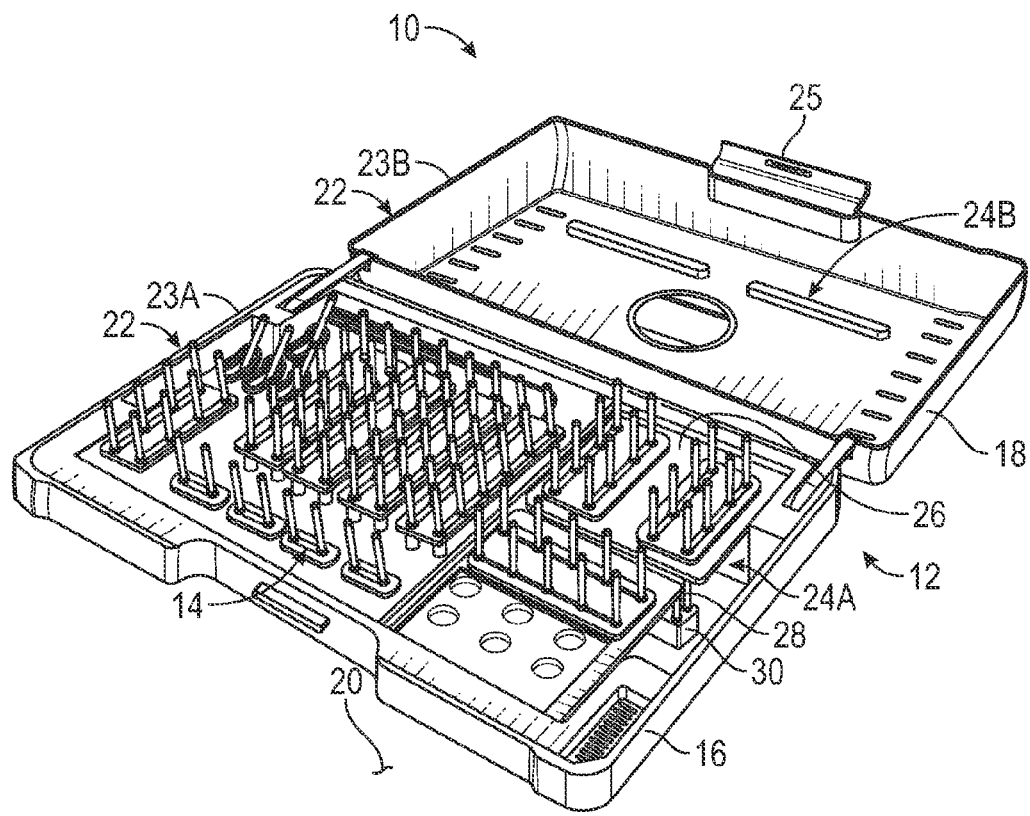
FIG. 1B is a perspective view of the dental tray of FIG. 1A in a second fully open position where both the lid and the base lay substantially flat, according to an example of the present disclosure.
Figure 1C:
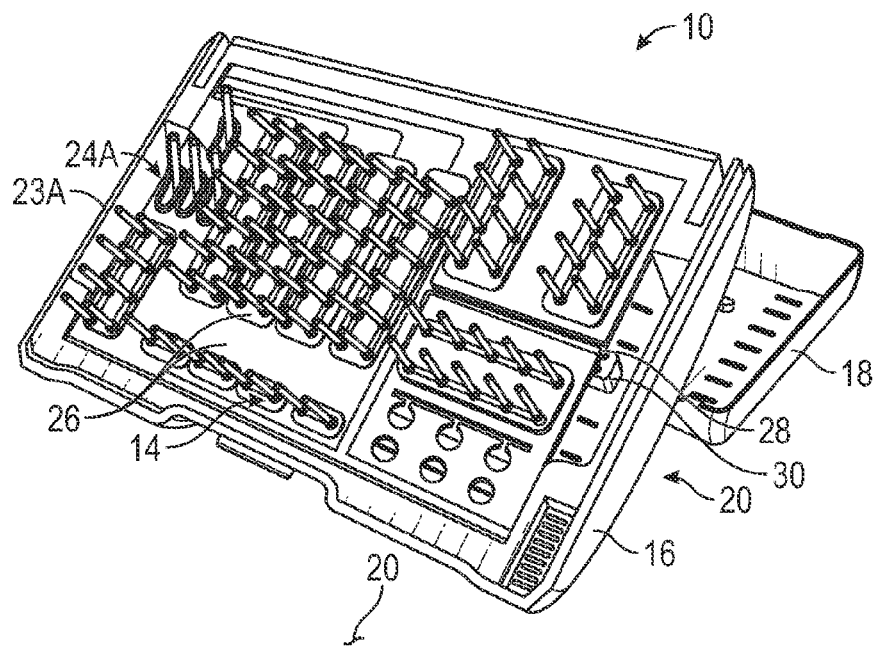
FIG. 1C is a perspective view of the dental tray of FIGS. 1A and 1B in a third propped position where the lid is angled relative to the base and partially rests thereon, according to an example of the present disclosure.
Figure 1D:
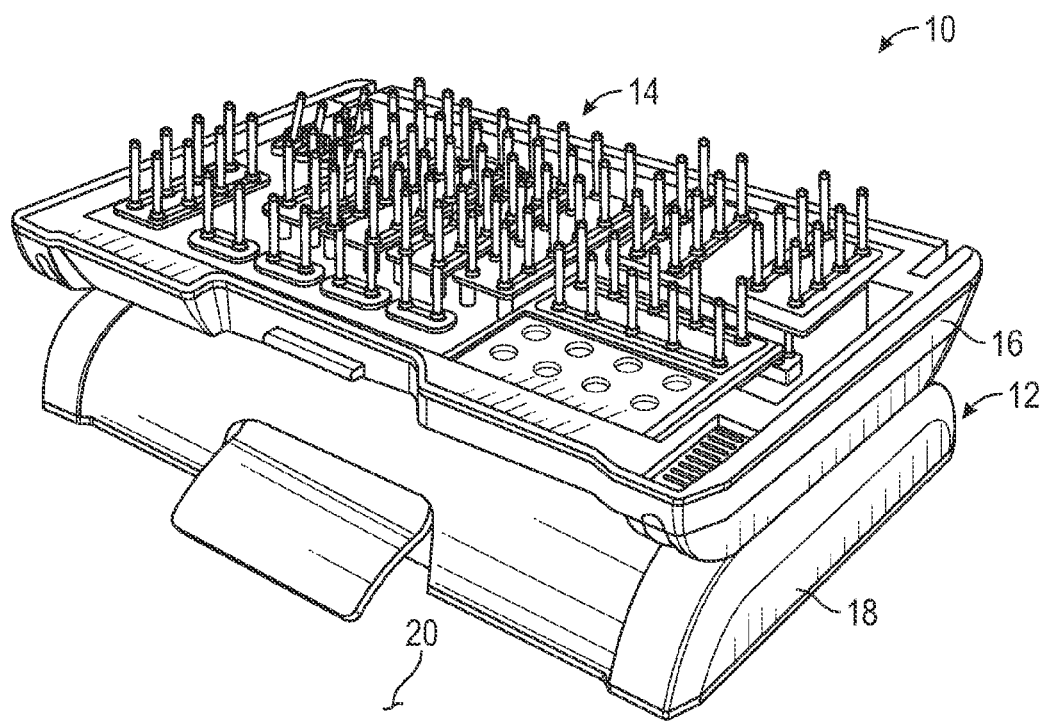
FIG. 1D is a perspective view of the dental tray of FIGS. 1A-IC in a fourth folded position where the lid is positioned under the base and the base rests atop the lid, according to an example of the present disclosure.

FIGS. 1A-1E show an example of a dental tray 10. The dental tray 10 can include a housing 12 and one or more tray inserts 14 (FIGS. 1B-1D). The housing 12 can include a base 16 and a lid 18.

As shown in FIGS. 1A-1E, the base 16 and lid 18 can be connected and can be moveable to a plurality of positions relative to one another to achieve different desired configurations. Some of these positions are illustrated in FIGS. 1A-1D and can include a closed position (FIG. 1A) where the lid 18 and the base 16 interface, a fully open position (FIG. 1B) where both the lid 18 and the base 16 lay substantially flat, a propped or easel position (FIG. 1C) where the lid 18 is angled relative to the base 16 and can rest partially on the base 16 as well as a surface and a folded position (FIG. 1D) where the lid 18 is positioned under the base 16 and the base 16 rests atop the lid 18. Thus, the base 16 and lid 18 are configured to be moveable relative to one another over 180 degrees, such that the base 16 can swap positions with the lid 18 (i.e. the base 16 can rest on a surface 20 as shown in FIG. 1A but can be moveable to the folded position of FIG. 1D so that the lid 18 rests on the surface 20 and the base 16 rests on the lid 18).

In view of the above positions, the dental tray 10 allows for opening to 180 degrees (FIG. 1B), propping up the drills at an angle like an easel for easier viewing and accessing of the dental surgical equipment such as the drills (FIG. 1C), folding the lid 18 all the way underneath the base 16 for adding height to the dental tray 10 and to move the lid 18 out of the way thereby reducing space taken up on the surface 20 of the sterile table, for example.

Referring now specifically to FIG. 1B, the lid 18 and base 16 can have a matching peripheral shape on first sides 22 thereof along rims 23A and 23B. These rims 23A and 23B can include rubber or another material designed to create a seal between the lid 18 and the base 16. This rim material can additionally help to prevent the lid 18 from sliding when the lid 18 is moved to the folded position of FIG. 1D, for example.

The lid 18 and base 16 can be shaped having interior portions 24A, 24B. The lid 18 and base 16 can be closed together such as in the position of FIG. 1A with a latch 25 or similar mechanical closure mechanism. The housing 12 (one or both of the lid 18 and the base 16) can be configured to hold the one or more tray inserts 14 along with other tools and components in the interior portions 24A, 24B. The housing 12 can comprise a hard shell designed to carry, organize and protect the one or more tray inserts 14. The housing 12 and/or the one or more tray inserts 14 can be constructed of suitable materials that are highly autoclave-temperature resistant such as plastics, composites, metal, etc. According to one example, the lid 18 and/or portions of the one or more tray inserts 14 can be constructed of a translucent material, an un-tinted transparent material such as a polycarbonate-plastic, or the like, to facilitate viewing by a user (i.e. through the lid 18 into the interior portions 24A, 24B and/or through the one or more tray inserts 14). With the interior portion 24B, the lid 18 can be configured to provide for additional instrument storage as needed.

As shown in FIGS. 1B and 1C, the one or more tray inserts 14 can be configured to be received within the housing 12 and can be removable therefrom. The one or more tray inserts 14 can include a first major surface 26 and one or more supports 28. The one or more supports 28 can extend below the first major surface 26 into the interior portion 24A and can be configured to couple with one or more mount feature(s) 30 of the housing 12 within the interior portion 24A. Such coupling can comprise any type of coupling known in the art including, for example, male/female, snap-fit, bayonet, interference, etc. Coupling of the one or more supports 28 with the mount feature(s) 30 can hold the one or more tray inserts 14 in place within the housing 12.

As illustrated in FIGS. 1B and 1C, for example, the supports 28 can position the first major surface 26 above the interior portions 24A so as to be flush with or adjacent the rim 23A, for example. The one or more supports 28 can comprise spaced legs for example, that can provide a space below the first major surface 26 for housing additional tools and instruments, for example. According to other examples, the one or more supports 28 can be located along a periphery of the one or more tray inserts 14 and can be configured to couple with the housing 12 adjacent the rim 23A. Although illustrated as all positioned within the base 16 in the examples of FIGS. 1B, 1C and 1D, according to further examples the one or more tray inserts 14 can be received by the lid 18 in a similar manner to that of the base 16.

Figure 1E:
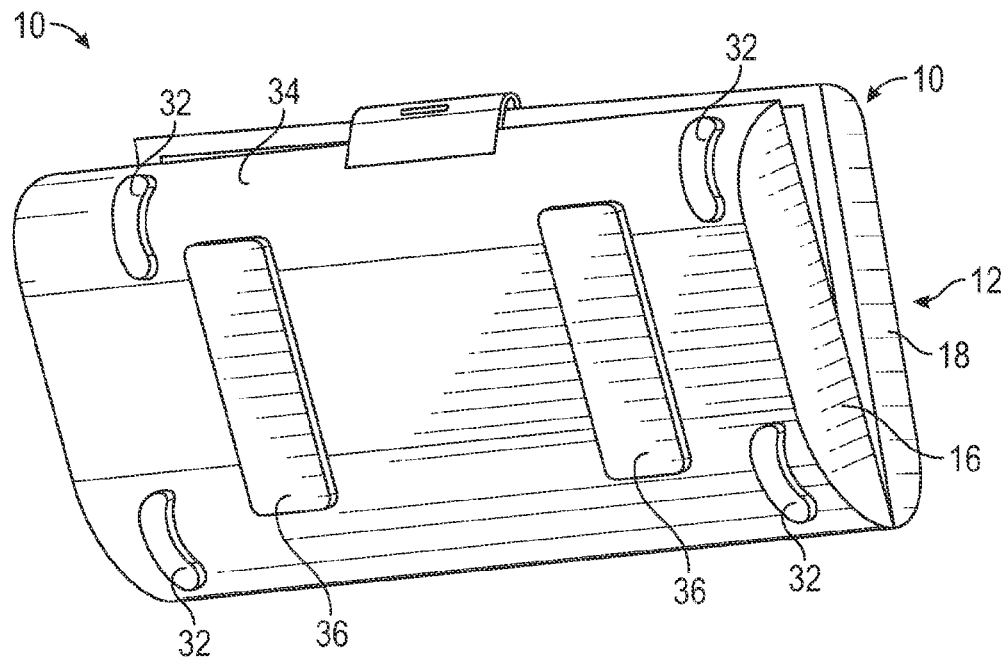
FIG. 1E is a perspective view of a base of the dental tray of FIGS. 1A-ID showing stabilizer feet and a drive mechanism according to an example of the present disclosure.
Figure 2A:
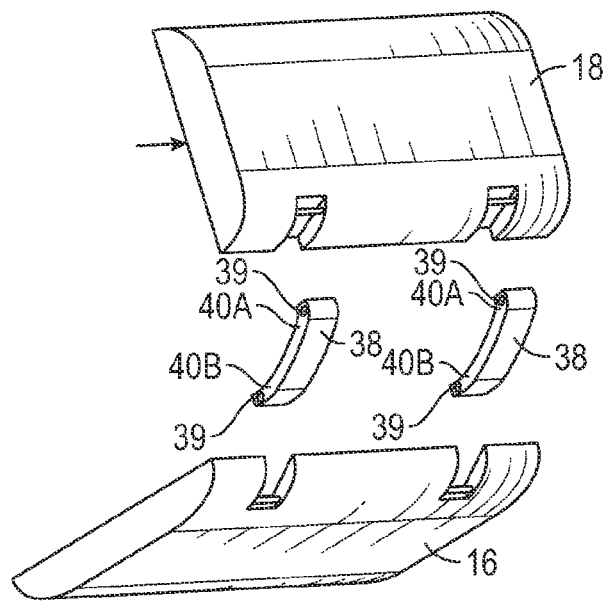
FIGS. 2A-2D show a hinge that connects the base with a lid of the dental tray and facilitates the various positions of the base and lid relative to one another, according to an example of the present disclosure.
Figure 2B:
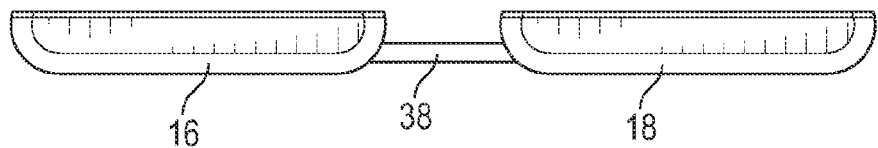
Figure 2C:
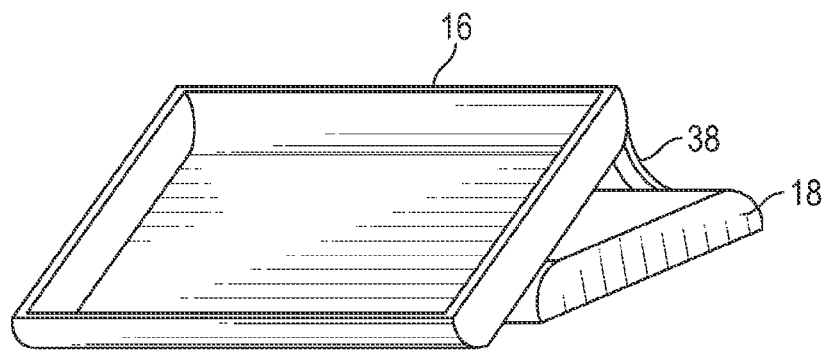
Figure 2D:
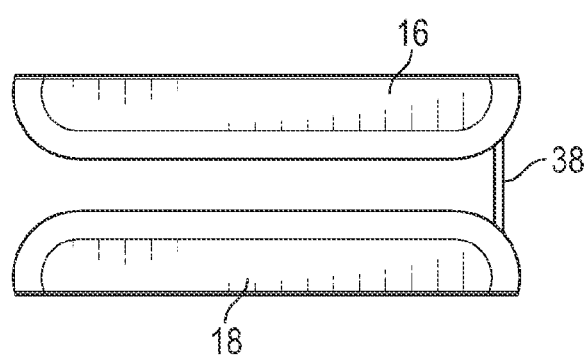

As illustrated in FIG. 1E, the base 16 can include feet 32 thereon. These can be designed of a material that can be compressible or a material of higher coefficient of friction than that of the housing 12 so as to prevent the base 16 from sliding on the surface 20. The feet 32 can extend along curved portions 34 of the exterior of the housing 12 so as to facilitate stabile positioning and prevent sliding when the base 16 is moved to the propped or easel position of FIG. 1C where the lid 18 is angled relative to the base 16 and can rest partially on the surface 20 via the feet 32.

According to the example of FIG. 1E, the dental tray 10, in particular, the base 16 can have a drive mechanism 36 configured to move the dental tray 10 along a predetermined cleaning pathway where the dental tray and the surgical instruments are cleaned according to a pre-defined protocol. More particularly, the drive mechanism 36 can comprise treads, wheels or the like that project through the housing 12 that can move the dental tray 10 along surface(s) to the cleaning location. The drive mechanism 36 can also include electro-mechanical drive (e.g., an electrical motor), pneumatic drive, hydraulic drive or another type of actuator known in the art.

Thus, according to some examples the dental tray 10 can follow a pre-set pathway through the cleaning process using the built-in drive mechanism 36 on the base 16. After a user reloads soiled dental surgical components into the dental tray 10, the dental tray 10 driven by the drive mechanism 36 can follow the pre-defined cleaning protocol (e.g., the dental tray 10 pauses in a rinse step for the user defined amount of time, then moves to the ultrasonic bath with pause for the user defined amount of time, then moves into autoclave for sterilization). According to some examples, the dental surgical tray pathway can include a step where the dental tray 10 docks and recharges after sterilization. The dental tray 10 can remain charged and can maintain sterile components during storage, waiting for a next use in another surgical procedure.

As discussed previously, the latch 25 can couple the lid 18 with the base 16 in the closed position of FIG. 1A. Additionally, the dental tray 10 can include a hinge 38 as further illustrated in FIGS. 2A-2D.

As shown in FIGS. 2A-2D, the hinge 38 can connect the base 16 with the lid 18 in a manner such that they are moveable to a plurality of positions including those of FIGS. 1A-1D, for example. In particular, the hinge 38 can have a pivot connection 39 at a first end 40A and a second end 40B. Thus, the hinge 38 can be pivotably connected at both the first end 40A and the second end 40B thereof such that the lid 18 and the base 16 are pivotable relative to one another via the hinge 38 to a plurality of positions (e.g., including those illustrated in FIGS. 1A-1D and FIGS. 2B-2D).

Figure 3:
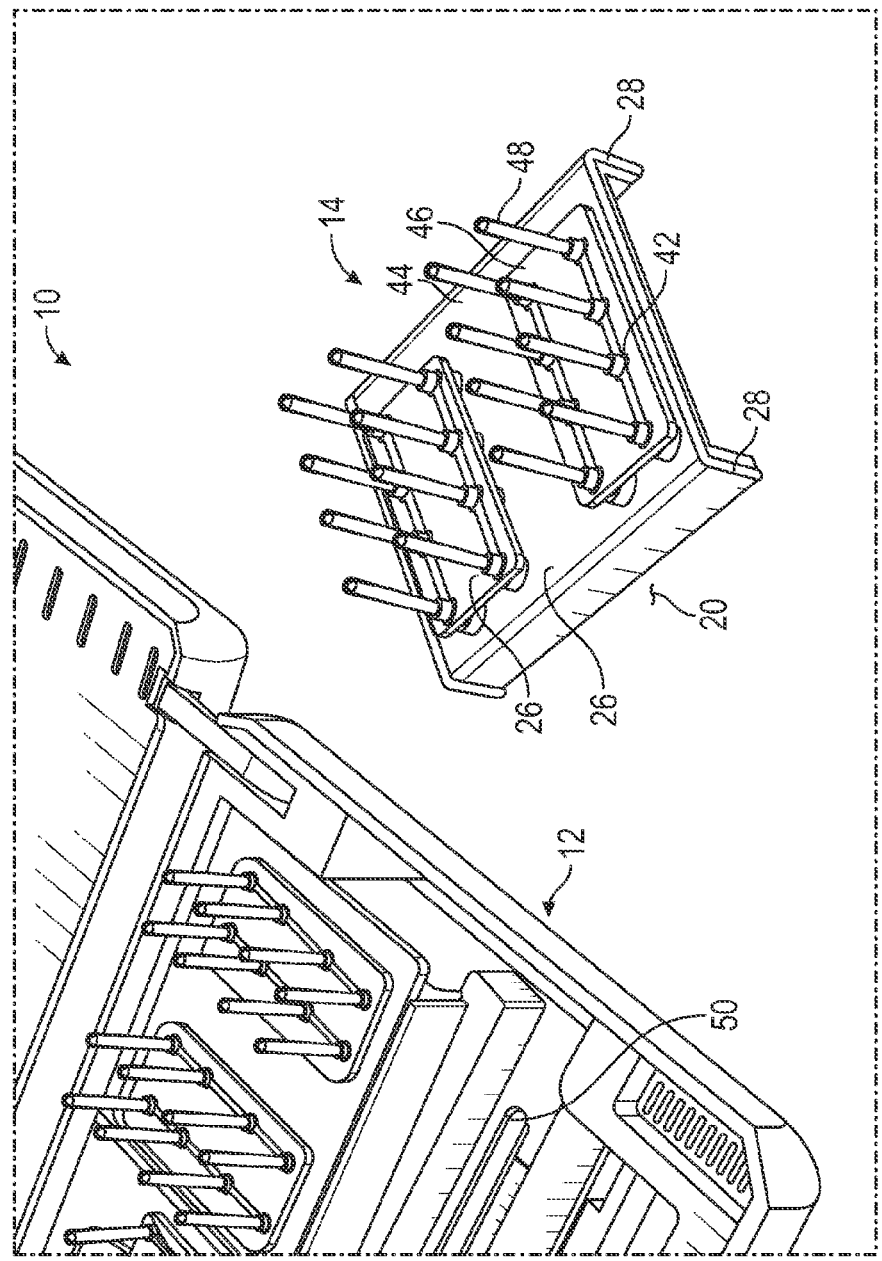
FIG. 3 is a perspective view of a tray insert removed from the dental tray and placed on a surface separate from the dental tray for use as a standalone module during a surgical procedure according to an example of the present disclosure.
Figure 4:
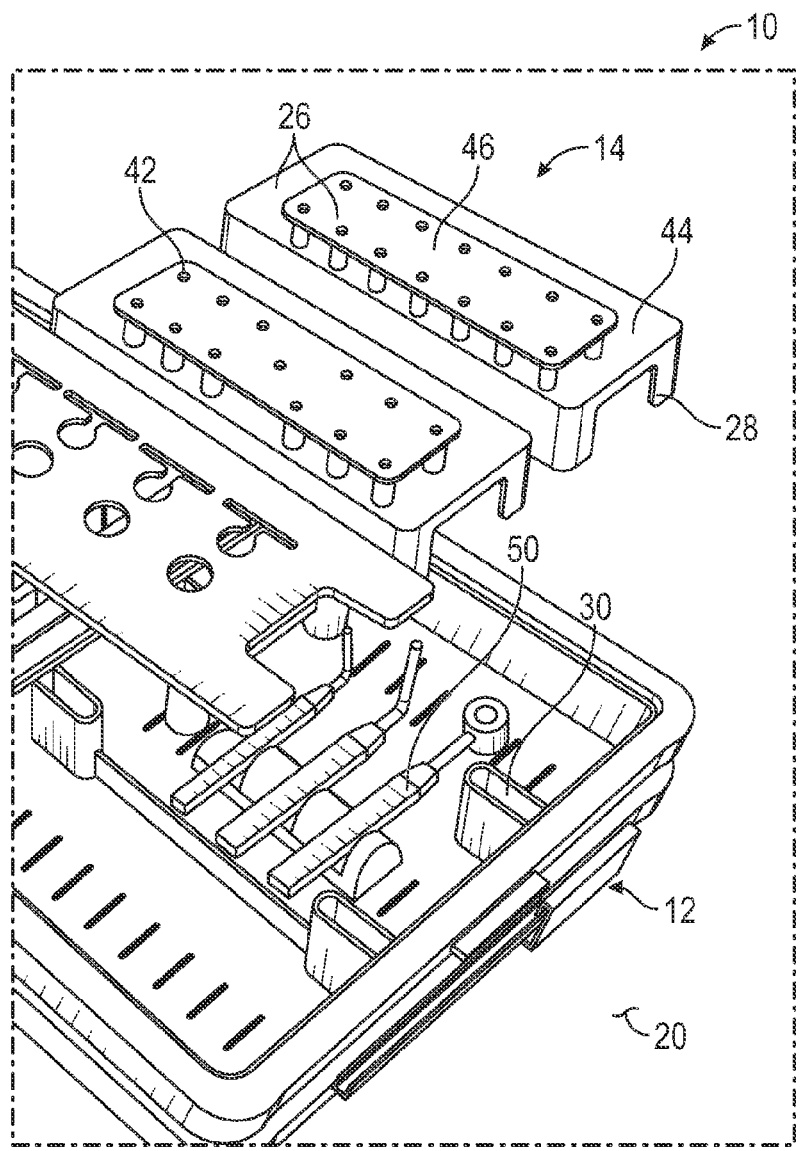
FIG. 4 is a perspective view of a plurality of tray inserts being removed from the dental tray and further illustrating dental surgical components being received in a housing of the dental tray below the plurality of tray inserts according to an example of the present disclosure.

FIGS. 3 and 4 show the one or more tray inserts 14 in further detail including the first major surface 26 and one or more supports 28 and further including a plurality of receptacles 42. In the example of FIG. 3, the one or more tray inserts 14 can be removable from the housing 12 and can be configured with the one or more supports 28 so as to be positionable exterior to and independent of the housing 12 by resting on the surface 20. Thus, the one or more tray inserts 14 can be used as a standalone unit during the surgical procedure independent of the remainder of the dental tray 10.

According to the example of FIGS. 3 and 4, the one or more tray inserts 14 can include at least a first portion 44 and a second portion 46. The second portion 46 can be constructed of a different material from that of the first portion 44 and can have the plurality of receptacles 42 (i.e. grommets) therein. These plurality of receptacles 42 facilitate reception and retention of surgical instruments 48. The construction of the second portion 46 will be discussed in further reference to FIGS. 11 and 12. The second portion 46 can be removable from the first portion 44 according to some examples.

The first portion 44 and/or second portion 46 can be constructed of a translucent material (e.g., can be color coded), an un-tinted transparent material, or the like, to facilitate viewing by a user of further surgical instruments 50 housed beneath the one or more tray inserts 14 when the one or more tray inserts 14 are positioned within the dental tray 10. This alleviates the user from having to pick up or otherwise move the one or more tray inserts 14 to review the further surgical instruments 50 housed beneath the one or more tray inserts 14. According to further examples, either the first portion 44 or the second portion 46 can be color coded with a color scheme that identifies particular ones of the surgical instruments 48 and/or the further surgical instruments 50 according to a step in the procedure.

FIGS. 3 and 4 show an example where the first portion 44 has the one or more supports 28. Together the first portion 44 and the second portion 46 can form the first major surface 26. As shown in FIG. 4, the one or more mount feature(s) 30 of the housing 12 can have different orientations and configurations and can be configured to facilitate coupling with different of the one or more tray inserts 14. This can allow positions of the one or more tray inserts 14 to be changed (e.g., swapped or otherwise substituted) as desired when received in the housing 12. FIG. 4 also shows the further surgical instruments 50 received below the one or more tray inserts 14 within the housing 12.

The one or more tray inserts 14 can each be treated as standalone module (e.g. each can have their own one or more supports 28), then each of the one or more tray inserts 14 can be sterilized independently from the rest of the dental tray 10. As discussed briefly above, the orientation of the one or more tray inserts 14 can be fully customizable (e.g., particular ones of the one or more tray inserts 14 representing different surgical sequences for different implant diameters or guided surgery can be snapped or otherwise coupled with the housing 12 in any order desired by the user. In some cases, some or all of the one or more tray inserts 14 can be stored in a compact manner, such as in a box (not shown) similar to a file storage box, when not in use and can be selected and selectively coupled to the housing 12 as desired according to the procedure.

Figure 5:
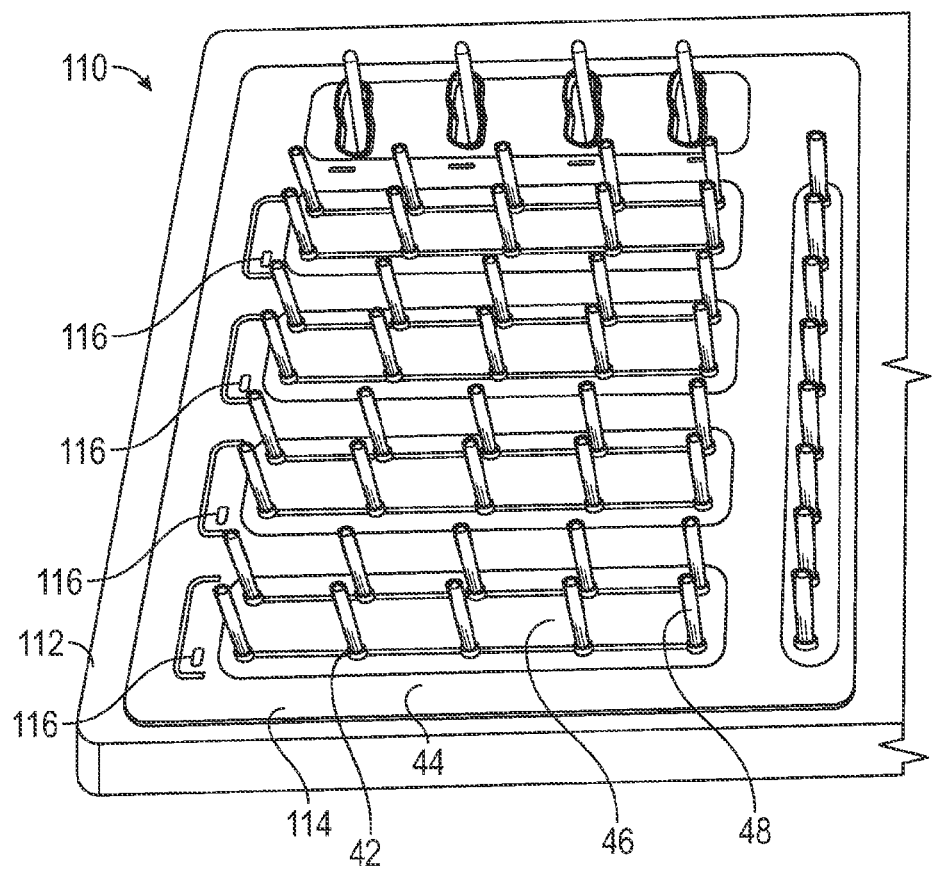
FIG. 5 is a perspective view of the dental tray with a plurality of indicators on the tray inserts corresponding to a set of surgical instruments that should be selected for use according to the dental procedure according to an example of the present disclosure.
Figure 6:
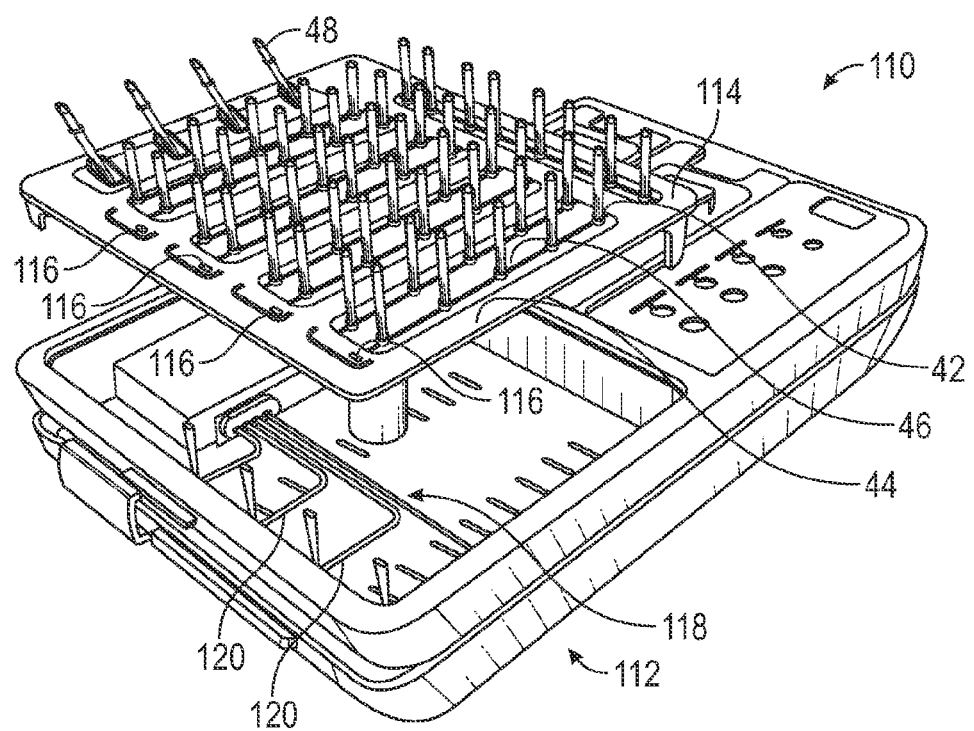
FIG. 6 is a perspective view of the tray inserts removed so as to illustrate a light pathway that pass under the tray inserts and along the housing of the dental tray according to an example of the present disclosure.
Figure 7:
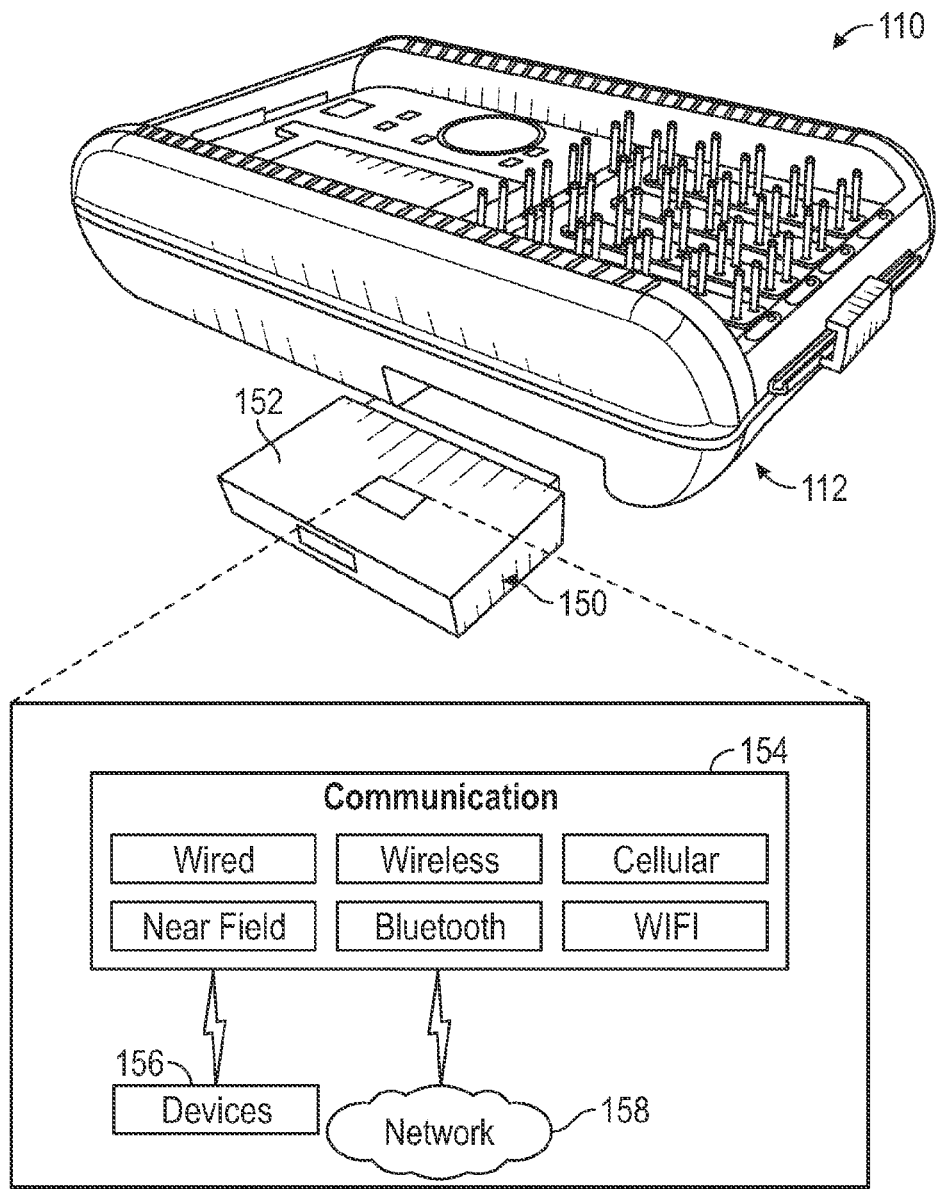
FIG. 7 is a partially schematic view of a removable and insertable unit such as a module that can be used such as to provide the lighting, control, communication and/or power to the dental tray according to an example of the present disclosure.

FIGS. 5-7 show examples of a dental tray 110 similar in construction to the dental tray 10 previously described unless otherwise noted. The example of FIGS. 5-7 can include a housing 112 and one or more tray inserts 114. The one or more tray inserts 114 can include a plurality of indicators 116 (FIGS. 5 and 6). The plurality of indicators 116 can be illuminated according to a desired surgical protocol (e.g., a drilling sequence), for example. In particular, as shown in FIG. 6, the dental surgical tray 110 can have a pathway 118 comprising electrically conductive wire and/or light conducting elements 120 (e.g., light pipes, optical fiber, etc.) extending within the housing 112. These plurality of light conducting elements 120 can be designed to transmit light therethrough. If wire or another electrically conductive element is utilized, they can be coupled to an LED or another light source that can provide the plurality of indicators 116. The wire can provide a pathway for electrical current for illuminating such light source. The pathway 118 can extend to at least one of the one or more tray inserts 114 and can couple with the plurality of indicators 116, for example. The pathway 118 can be configured to illuminate the indicators 116 so as to illuminate one or more areas of the one or more tray inserts 114 according to the surgical protocol to indicate a one or plurality of the surgical instruments 48 should be selected according to a step of the surgical protocol. Put another way, the plurality of light conducting elements 120 can terminate at or adjacent the at least one of the one or more tray inserts 114 so as to illuminate and indicate a particular one or particular set of the plurality of receptacles 42.

FIGS. 5 and 6 show the first portion 44 (single unit) and a plurality of second portions 46 of the one or more tray inserts 114. The plurality of second portions 46 can have the plurality of receptacles 42 receiving the surgical instruments 48. The first portions 44 can have a corresponding one of the plurality of indicators 116 associated therewith so as to indicate a particular set of the surgical instruments 48 appropriate for the procedure. This can be done by the proximity of the indictor 116 and by color coding of the second portion 46 and/or first portion 44, for example. Thus, the indicator 116 can illuminate which row of the surgical instruments 48 should be used next in the next drill sequence, for example. However, according to other examples light can be directed by the pathway 118 to a particular one or sets of the plurality of receptacles 42 so as to illuminate the particular one or sets of the plurality of receptacles 42 (example shown in FIGS. 9 and 10).

FIG. 7 shows an example where a unit 150 is utilized and is operably coupled to the light conducting elements 120 and the pathway 118 (FIG. 6). The unit 150 can include, for example, a module 152 that can include a light source(s), a controller and a battery. The module 152 can be configured to be insertable and removable from the housing 112 for external charging, sterilization and other use. However, according to other examples the unit 150 can include the light source(s), the battery, a communication unit 154 and/or the controller. The communication unit 154 can communicate with devices 156 using known communication modalities both wired and wireless. Such communication modalities include, but are not limited to near field (e.g., RFID, NFC, etc.), Bluetooth, cellular, Wi-Fi, etc. The devices 156 contemplated include, but are not limited to, an RFID module including an electronic use monitoring unit, a surgical guide configured to guide a dental drill during the surgical procedure and/or a mobile device running a software application. According to further examples, data (e.g., surgical protocol instructions, etc.) can be transmitted to the unit 150 can be from a computer network 158 and/or the devices 156, for example. Data can be gathered by the unit 150 and can be stored on the computer network 158, transmitted to the devices 156, etc. for example.

According to one example, the unit 150 can comprise a compatible unit that can be connected to the dental tray 110 to provide power, light, and programmed instructions based on the implant chosen for placement. According to further examples with the unit 150 as the compatible unit, the unit 150 can be configured to scan dental implant packaging in order for the proper implant program to be selected automatically by the controller (e.g., the user can scan the dental implant packaging to smart select the program that dictates the light pathway showing the drill pathway on the dental tray 110 as well as the proper drill speeds on the drill unit).

According to yet another example, the unit 150 can provide drill use tracking as a feature, e.g. by utilizing flash memory for RFID drill counting/monitoring. The benefit can be to provide automated tracking of surgical instruments(s) 48 usage so that a clinician knows when the recommended number of uses for a given one of the surgical instruments 48 has been reached and that it is time to replace that surgical instruments 48. Alternatively, wear indicating filaments can be included within the tray to provide a visual queue that drills have been used and/or sterilized multiple times. Alternatively, the grommets can contain sensors to count number of times drills or instruments have been removed or replaced.

According to yet a further example, the unit 150 can be used by the dental assistant when re-loading the dental tray 110 with the surgical instruments 48 after the surgical instruments 48 are cleaned separate for the dental tray 110. In this example, a mobile application stored and run on the device 156 (for example on a mobile smart phone, tablet, etc.), can be connected to the light source for the light conducting elements 120 (FIG. 6). According to this example, the camera of the device 156 can be used to scan identifying marks on the surgical instruments 48 and the mobile application can use these identifying marks to illuminate a correct receptacle in the one or more tray inserts 114 for the selected and scanned one of the surgical instruments 48. The application can also track how many times the surgical instruments 48 has been cleaned and reloaded in to the dental tray 110. This number of cleanings and/or reloading can be used as an indicator of when the surgical instruments 48 are in need of replacement. In another example, the mobile app can automatically interface via the network 158, for example, with a manufacturer's e-commerce system to order a new instrument.

According to a further example, the dental tray 110 and the surgical instruments 48 can be scanned using a bar code scanner that is part of the unit 150 or the device 156. The bar codes read by the scanner can be the Unique Device Identification "UDI" codes on the surgical instruments 48, for example, if direct part marking are utilized. The bar code scanner can be an application for a mobile device such as a smart phone, for example. The software application can compare the bar code to assure all instruments are present and in the right location in the dental tray 110.

In a further example, the application runs through a standard dental tray loading sequence rather than scanning each of the surgical instruments 48. The application can display a picture of each of the surgical instruments 48 on the mobile device and can work with the pathway 118 (FIG. 6) to illuminate the proper location in the dental tray 110. The bar code scanning function can be employed if there is uncertainty regarding the identification of the instrument and error proofing can be used at the conclusion of tray loading to verify the proper location of each of the surgical instruments 48, for example. It is contemplated the mobile device (e.g., smart phone, tablet, etc.) can be placed in a clear sleeve that can be secured with zip lock or similar mechanism. The sleeve can prevent the mobile device from becoming contaminated during the cleaning of the instruments.

Figure 8:
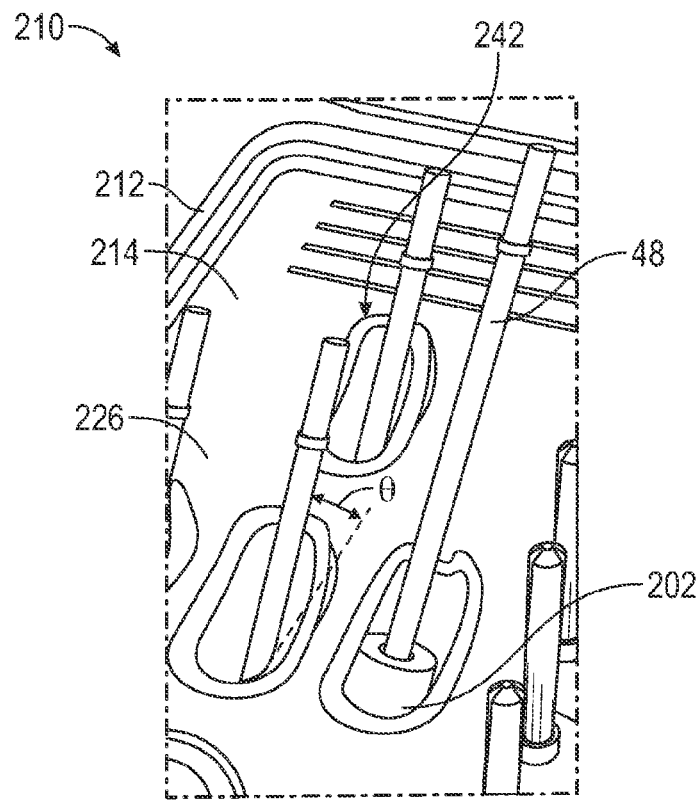
FIG. 8 is a perspective view of a portion of a tray insert having a receptacle angled relative to a major surface of the tray insert and having an actuator mechanism to move one of the surgical instruments for identification and/or ease of access according to an example of the present disclosure.

FIG. 8 shows another example of a dental tray 210 similar in construction to the dental tray 10, 110 previously described unless otherwise noted. The example of FIG. 8 can include a housing 212 and one or more tray inserts 214. The one or more tray inserts 214 can include a first major surface 226 and a plurality of receptacles 242. As shown in the example of FIG. 8, the plurality of receptacles 242 can be angled relative to the first major surface 226 such that the surgical instruments 48 when received in the plurality of receptacles 242 are positioned at an acute angle $\theta$ relative to the first major surface 226. In this manner, sharp ends of the surgical instruments 48 can be pointed away from the user (e.g. angled down into the one or more tray inserts 214) with the ISO latch on the shank of the surgical instruments 48 available for pickup using a hand piece or driver, for example.

The example of FIG. 8 additionally shows an actuation mechanism 202 configured to apply a force that moves one or more of the plurality of receptacles or one or more of the surgical instruments 48 to elevate the one or more of the surgical instruments 48 relative to others for at least one of identification and ease of coupling with a dental surgical tool. The actuation mechanism 202 comprises a pneumatically driven actuator, for example. A pneumatic tube can run parallel to the pathway 118 (FIG. 6) previously described and illustrated herein. The pneumatics utilized can be powered by a gas supply commonly used to run high speed dental hand pieces, for example.

According to some example, an entire drill sequence for a given implant can be elevated using the actuation mechanism 202. In other cases, the proper one of the surgical instruments 48 in the surgical sequence can be elevated to reduce the number of actuators.

Figure 9:
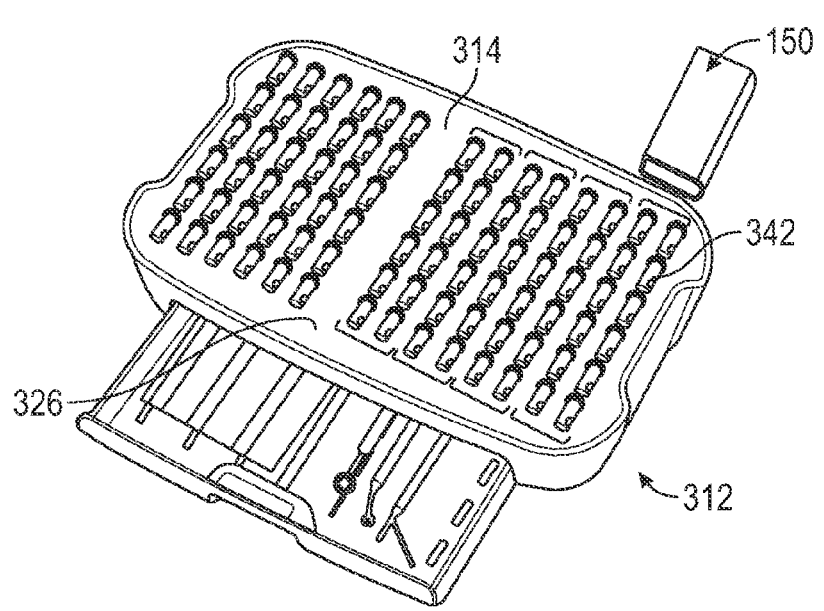
FIGS. 9 and 10 are a perspective view of the dental tray having a receptacle angled relative to a major surface of the tray insert and having a light identifier within one or more of the plurality of receptacles according to an example of the present application.
Figure 10:
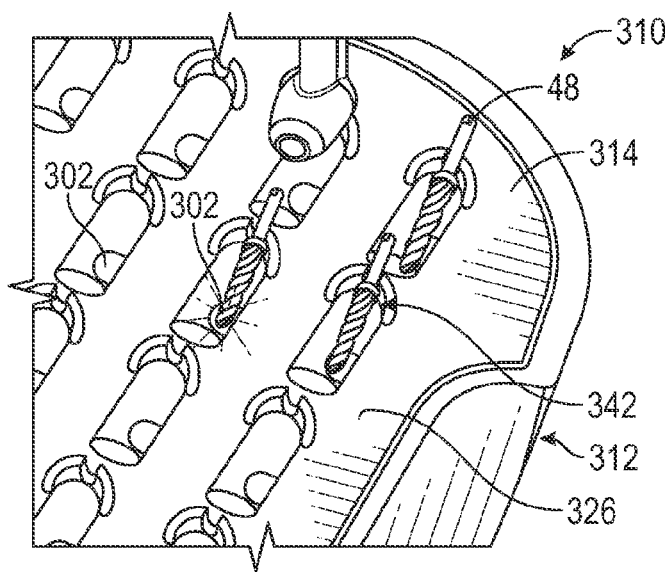

FIGS. 9 and 10 show another example of a dental tray 310 similar in construction to the dental tray 10, 110, 210 previously described unless otherwise noted. The example of FIGS. 9 and 10 can include a housing 312 and one or more tray inserts 314. The one or more tray inserts 314 can include a first major surface 326 and a plurality of receptacles 342. Similar to the example of FIG. 8, FIG. 10 shows the plurality of receptacles 342 can be angled relative to the first major surface 326 such that the surgical instruments 48 when received in the plurality of receptacles 342 are positioned at an acute angle θ relative to the first major surface 326.

FIGS. 9 and 10 also show an example where one or more identifiers 302 can be utilized to illuminate one or more of the plurality of receptacles 342 for selecting a correct one or plurality of the surgical instruments 48 according to the surgical procedure.

Similar to the example of FIG. 7, the examples of FIGS. 8-10 can utilize the unit 150 (shown in FIG. 9) and the device(s) 156, etc. as previously described. These can be used for controlling the illumination of the one or more of the plurality of receptacles 342 and/or for controlling pneumatic valves to control operation of the actuation mechanism 202 as desired. The dental tray 210 and/or the dental tray 310 can utilize the removable module as previously described or can have a connecting cable with fiber optics and pneumatic tubes connects to a port in the dental tray.

Figure 11:
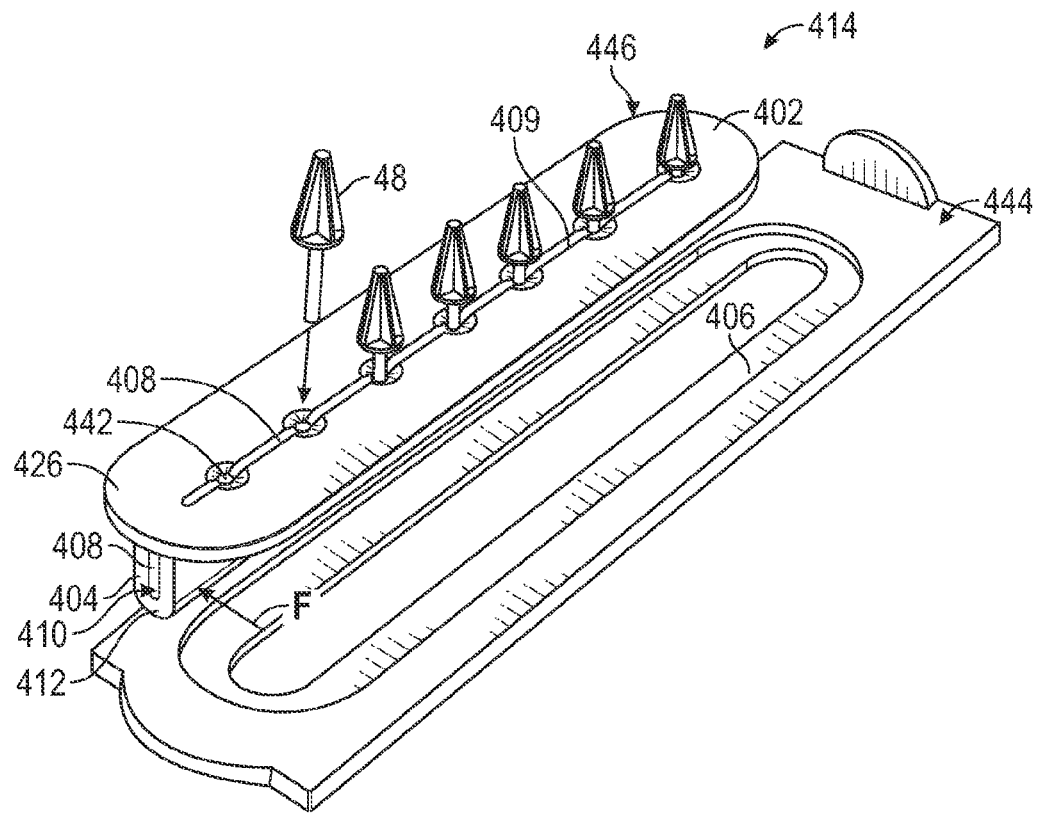
FIG. 11 is a perspective view of a tray insert having at least two portions one portion can be removable from the other portion and can have a channel connecting a plurality of grommets according to an example of the present application.
Figure 12:
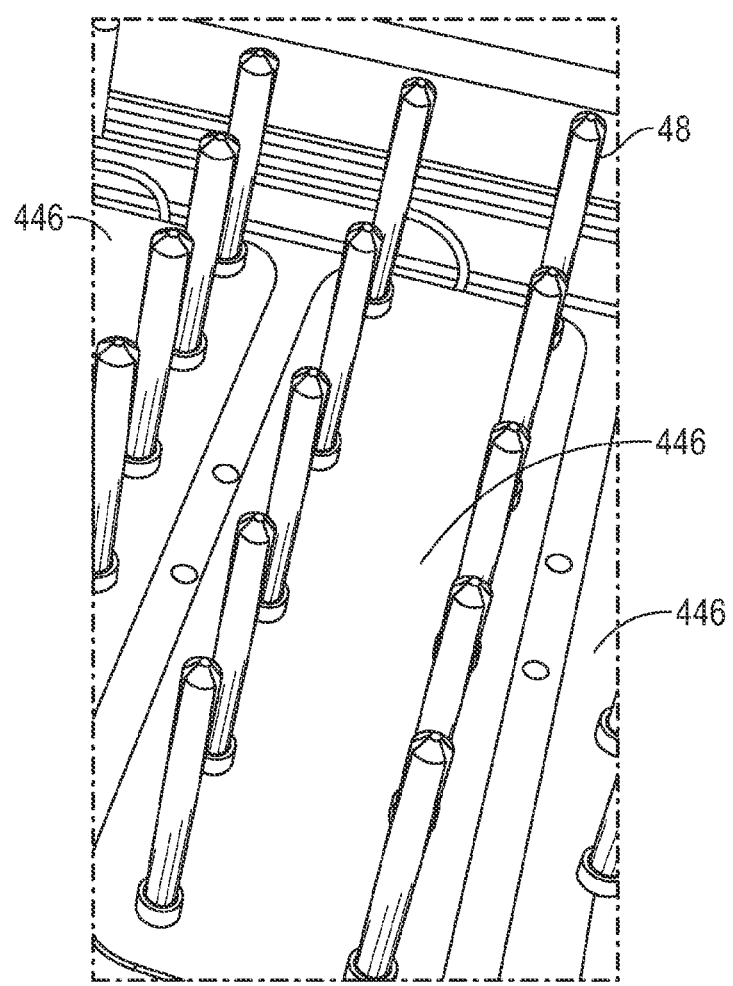
FIG. 12 is a perspective view of a plurality of the tray inserts of FIG. 11 being used within the dental tray according to an example of the present application.

FIGS. 11 and 12 show the one or more tray inserts 414 according to another aspect. Recall that according to some examples, the one or more tray inserts 414 can include at least a first portion 444 and a second portion 446 according to some examples. The second portion 446 can be constructed of a different material from that of the first portion 444 and can have the plurality of receptacles 442 (i.e. holes) therein. These plurality of receptacles 442 facilitate reception and retention of surgical instruments 48 via a shank thereof. As shown in FIG. 11, the second portion 446 can be removable from and insertable in the first portion 444.

FIG. 11 shows the second portion 446 can include a first flange part 402 and a second retention part 404. The flange part 402 can be connected to the retention part 404 as a single piece such as by molding, for example. The flange part 402 and/or the retention part 404 can be made of silicone or another elastomeric material that can expand and contract as needed by the size the drill/instrument shank. The flange part 402 can form at least a portion of the first major surface 426 and can have the plurality of receptacles 442 extending therethrough. The flange part 402 with the first major surface 426 can act as a stop for the surgical instruments 48 and can be configured to seat down on the first portion 444 such as in a recess 406. Together the flange part 402 and the retention part 404 can form a channel 408 that extends along the flange part 402 and has a slit opening 409. The channel 408 can also extend along the retention part 404. The channel 408 communicates with the plurality of receptacles 442. Thus, the plurality of receptacles 442 can communicate with one another via the channel 408. The retention part 404 can have a U-shape in cross-section with the interior of the U forming a part of the channel 408. The retention part 404 can have an opening 410 to the channel 408 at a least one end 412 thereof. The retention part 404 can be constructed of a plastic or other elastomeric material and can be configured to exert a bias closing force F (due to the material and the U-shape) on the surgical instruments 48 that extend into the channel 408 from the plurality of receptacles 442.

FIG. 12 shows a plurality of the second portions 446 can be utilized.

These portions 446 can organize the surgical instruments 48 into various sets of instruments. The second portions 446 can be color coded, have indicators, etc. as discussed above with other examples.

Use of the channel 408 can facilitate cleaning of the second portions 446 including within the plurality of receptacles 442. Cleaning can be improved because a whole second portion 446 including multiple of the plurality of receptacles 442 can be removed, cleaned and then replaced in a single effort as compared to removing, cleaning and replacing multiple individual grommets. Ease of cleaning can encourage users to clean the plurality of receptacles 442 more frequently and thoroughly.

Furthermore, the channel 408 can allow for increased holding stability for larger and smaller diameter shanks of the surgical instruments 48. The holding stability would also be increased for shanks of the surgical instruments 48 that are larger or smaller than the standard shank for which an individual one of the plurality of receptacles 442 is designed. In current surgical trays, some smaller components can be captured in a manner that is loose, and therefore, run the risk of falling out. Alternatively, with current surgical trays, some larger components can be captured in a manner such that they are difficult to remove from the tray as they are too tightly retained. The channel 408 design can allow for small diameter shanks to be held securely with elastic expansion and can also allow for elastic expansion to securely hold larger diameter shanks.

The example of FIG. 7 is described herein as including one or more of units, devices, networks, and/or modules. Modules and/or units in the context of FIG. 7 may constitute either software modules or units (e.g., code embodied on a machine-readable medium or in a transmission signal) or hardware. A module and/or unit as used herein is a tangible unit capable of performing certain operations and may be configured or arranged in a certain manner. In examples, one or more computer systems (e.g., a standalone, client or server computer system) or one or more modules of a computer system (e.g., a processor or a group of processors) may be configured by software (e.g., an application or application portion) as a module and/or unit that operates to perform certain operations as described herein.

In the example of FIG. 7, a module and/or unit may be implemented mechanically or electronically. For example, a module and/or unit may comprise dedicated circuitry or logic that is permanently configured (e.g., as a special-purpose processor, such as a field programmable gate array (FPGA) or an application-specific integrated circuit (ASIC)) to perform certain operations. A module and/or may also comprise programmable logic or circuitry (e.g., as encompassed within a general-purpose processor or other programmable processor) that is temporarily configured by software to perform certain operations. It will be appreciated that the decision to implement a module and/or mechanically, in dedicated and permanently configured circuitry, or in temporarily configured circuitry (e.g., configured by software) may be driven by cost and time considerations.

Accordingly, the term "module" and/or "unit" in the context of FIG. 7 can be understood to encompass a tangible entity, such as hardware, that can be an entity that is physically constructed, permanently configured (e.g., hard-wired) or temporarily configured (e.g., programmed) to operate in a certain manner and/or to perform certain operations described herein. Considering examples in which modules and/or units are temporarily configured (e.g., programmed), each of the modules and/or units need not be configured or instantiated at any one instance in time. For example, where the modules and/or unit comprise a general-purpose processor configured using software, the general-purpose processor may be configured as respective different modules and/or units at different times. Software may accordingly configure a processor, for example, to constitute a particular module and/or unit at one instance of time and to constitute a different module and/or unit at a different instance of time.

Modules and/or units can provide information to, and receive information from, other modules and/or units. Accordingly, the described modules and/or units may be regarded as being communicatively coupled. Where multiple of such modules and/or units exist contemporaneously, communications may be achieved through signal transmission (e.g., over appropriate circuits and buses) that connect the modules and/or units. In examples in which multiple modules and/or units are configured or instantiated at different times, communications between such modules and/or units may be achieved, for example, through the storage and retrieval of information in memory structures to which the multiple modules and/or units have access. For example, one module may perform an operation, and store the output of that operation in a memory device to which it is communicatively coupled. A further module may then, at a later time, access the memory device to retrieve and process the stored output. Modules and/or units may also initiate communications with input or output devices, and can operate on a resource (e.g., a collection of information).

The various operations of example systems described herein may be performed, at least partially, by one or more processors that are temporarily configured (e.g., by software) or permanently configured to perform the relevant operations. Whether temporarily or permanently configured, such processors may constitute processor-implemented modules and/or units that operate to perform one or more operations or functions. The modules and/or units referred to herein may, in some examples, comprise processor-implemented modules and/or units.

Similarly, the systems described herein may be at least partially processor-implemented. For example, at least some of the operations of a method or system may be performed by one or more processors or processor-implemented modules and/or units. The performance of certain of the operations may be distributed among the one or more processors, not only residing within a single machine, but deployed across a number of machines. In the example of FIG. 7, the processor or processors may be located in a single location (e.g., within a home environment, an office environment or as a server farm), while in other examples the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., Application Program Interfaces (APIs).)

Examples may be implemented in digital electronic circuitry, or in computer hardware, firmware, software, or in combinations of them. Examples may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In examples, operations may be performed by one or more programmable processors executing a computer program to perform functions by operating on input data and generating output. Method and/or system operations can also be performed by, and apparatus of examples may be implemented as, special purpose logic circuitry, e.g., a field programmable gate array (FPGA) or an application-specific integrated circuit (ASIC).

The computing system can include clients and servers. A client and server are generally remote from each other and typically interact through a communication network. The relationship of client and server arises by virtue of computer programs running on the respective computers and having a client-server relationship to each other. In examples deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. Also, other medical professions can utilize similar type of sterilization trays that house multiple instruments. Any of the embodiments described herewith in would also be applicable to these trays and are not specifically limited to dental instruments and dental applications that are exemplary described. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed:

1. An instrument retaining element for a dental tray for use in a surgical procedure, comprising:
   a first part having a longitudinal length and defining a plurality of receptacles therein, wherein the plurality of receptacles are spaced from one another along the longitudinal length, the plurality of receptacles configured to receive a first shank section of a plurality of surgical instruments, wherein the first part defines a first part of a channel that extends along at least a portion of the longitudinal length and communicates with two or more of the plurality of receptacles; and
   a second part connected to the first part and having a longitudinal length, wherein the second part has a U-shape in cross-section through the longitudinal length of the second part with opposing walls that define a second part of the channel, wherein the second part of the channel communicates with the first part of the channel and the plurality of receptacles, and wherein the second part is configured to elastically expand thereby increasing a size of the second part of the channel to receive and retain a second shank section of the plurality of surgical instruments when the first section of the plurality of surgical instruments are received in the plurality of receptacles.

2. The retaining element of claim 1, further comprising a second component of the dental tray, wherein the first part is shaped as a flange and is removable from and insertable into the second component of the dental tray.

3. The retaining element of claim 1, wherein the first part has an exterior facing surface that comprises a stop for the plurality of surgical instruments when the plurality of surgical instruments are inserted in the plurality of receptacles.

4. The retaining element of claim 1, wherein the second part has a first opening for the channel at a first end thereof.

5. The retaining element of claim 4, wherein the first part has a second opening that comprises a slit for the channel.

6. The retaining element of claim 5, wherein at least one of the opening and the second opening allow for access to the channel for cleaning.

7. The retaining element of claim 1, wherein the second part is configured to exert a force on the plurality of surgical instruments to retain the plurality of surgical instruments within the second part of the channel.

8. The retaining element of claim 7, wherein the force is exerted by elastic expansion of the second part upon receiving the plurality of surgical instruments in the second part of the channel.

9. A medical tray for a surgical procedure, comprising:
   a housing; and
   one or more tray inserts configured to be received within the housing, wherein each of the one or more tray inserts includes an instrument retaining part that has a longitudinal length and is configured to receive and retain a plurality of surgical instruments via a plurality of receptacles and a channel formed therein, wherein the channel communicates with the plurality of receptacles along at least a portion of the longitudinal length and is expandable with elastic expansion of the instrument retaining part to receive one or more of the plurality of surgical instruments.

10. The medical tray of claim 9, wherein the instrument retaining part is configured to exert a force on the plurality of surgical instruments to retain the plurality of surgical instruments within the channel.

11. The medical tray claim 9, wherein the instrument retaining part comprises:
    a first part defining the plurality of receptacles and defining a first part of the channel;
    a second part connected to the first part and having a U-shape in cross-section, wherein the second part defines a second part of the channel that communicates with the first part of the channel and the plurality of receptacles, and wherein the second part of the channel is configured to receive a second section of the plurality of surgical instruments when a first section of the plurality of surgical instruments are received in the plurality of receptacles.

12. The medical tray of claim 11, further comprising a second component of the dental tray, wherein the first part is shaped as a flange and is removable from and insertable into the second component of the dental tray.

13. The medical tray of claim 11, wherein the first part has an exterior facing surface that comprises a stop for the plurality of surgical instruments when the plurality of surgical instruments are inserted in the tray insert.

14. The medical tray of claim 11, wherein the second part has a first opening for the channel at a first end thereof.

15. The medical tray of claim 14, wherein the first part has a second opening that comprises a slit for the channel.

16. The medical tray of claim 15, wherein at least one of the first opening and the second opening allow for access to the channel for cleaning.

17. The medical tray of claim 11, wherein the second part is configured to exert a force on the plurality of surgical instruments to retain the plurality of surgical instruments within the second part of the channel.

18. The medical tray of claim 17, wherein the force is exerted by elastic expansion of the second part upon receiving the plurality of surgical instruments in the second part of the channel.

19. The medical tray of claim 11, wherein the channel and the plurality of receptacles have corresponding openings at a first major surface of the instrument retaining element.

20. A medical tray for a surgical procedure, comprising:
a housing; and
one or more tray inserts configured to be received within the housing, wherein each of the one or more tray inserts includes an instrument retaining element having a longitudinal length and a plurality of receptacles and a channel formed therein, wherein the channel extends along at least a portion of the longitudinal length and communicates with the plurality of receptacles, wherein the instrument retaining element is configured to receive a plurality of surgical instruments via the plurality of receptacles and the channel, and wherein a part of the instrument retaining element that defines the channel is elastically expandable to exert a force on the plurality of surgical instruments to retain the plurality of surgical instruments within the channel.

* * * * *

UNITED STATES PATENT AND TRADEMARK OFFICE
CERTIFICATE OF CORRECTION

PATENT NO. : 10,987,205 B2
APPLICATION NO. : 16/591218
DATED : April 27, 2021
INVENTOR(S) : Jeffrey T. DeBord Page 1 of 1

It is certified that error appears in the above-identified patent and that said Letters Patent is hereby corrected as shown below:

In the Claims

In Column 16, Line 4, in Claim 6, after "of the", insert --first--

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*